United States Patent [19]

Menor

[11] Patent Number: 4,575,064
[45] Date of Patent: Mar. 11, 1986

[54] PATIENT TREATMENT TABLE

[75] Inventor: George Menor, Martinez, Calif.

[73] Assignee: Siemens Medical Laboratories, Inc., Walnut Creek, Calif.

[21] Appl. No.: 530,318

[22] Filed: Sep. 8, 1983

[51] Int. Cl.⁴ ............................................. A61G 13/00
[52] U.S. Cl. ..................................... 269/322; 378/209
[58] Field of Search .............. 269/322, 323, 324, 325, 269/326, 910, 242, 901; 378/195, 196, 209; 5/446

[56] References Cited

U.S. PATENT DOCUMENTS

| | | | |
|---|---|---|---|
| 2,188,433 | 1/1940 | Friese | 269/242 |
| 3,459,939 | 8/1969 | Walischmiller | 269/322 |
| 3,742,569 | 7/1973 | Moehlenpah | 269/910 |
| 4,236,599 | 12/1980 | Luff et al. | 269/901 |

Primary Examiner—Frederick R. Schmidt
Assistant Examiner—Judy J. Hartman
Attorney, Agent, or Firm—Mark H. Jay

[57] ABSTRACT

A patient treatment table has a base and a table plate upon which a patient may be positioned. A spine having two bars supports at least one part of the table. The bars are so mounted that they may be shifted towards and away from each other beneath the table plate while keeping the table plate unmoved.

10 Claims, 3 Drawing Figures

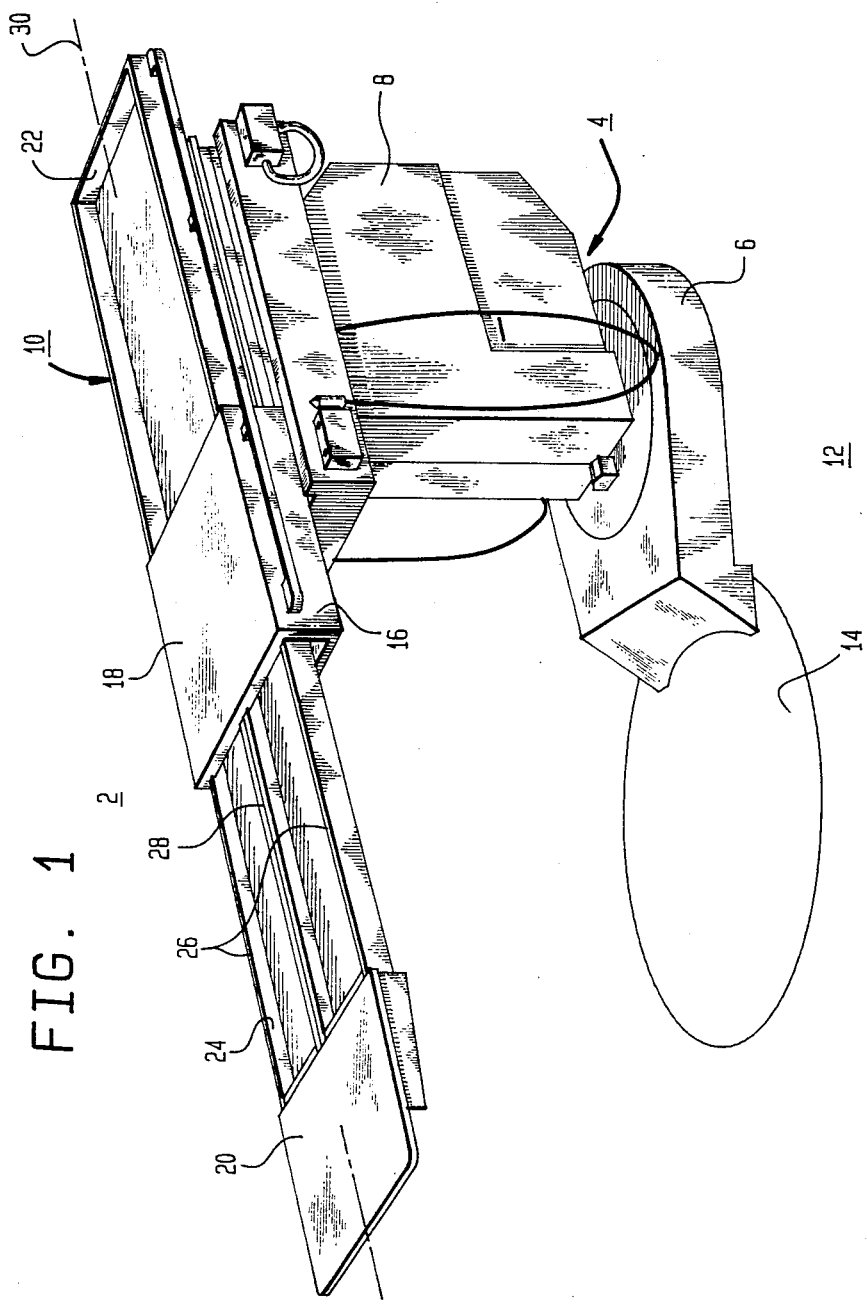

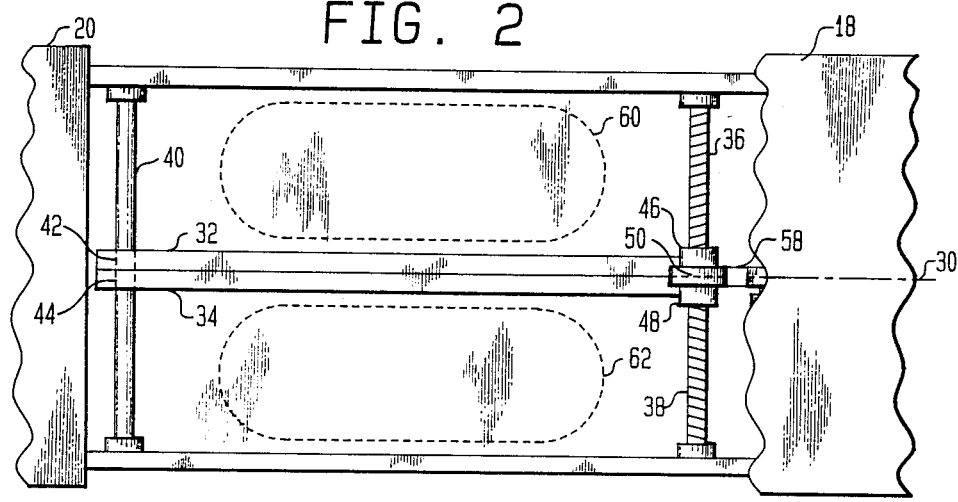
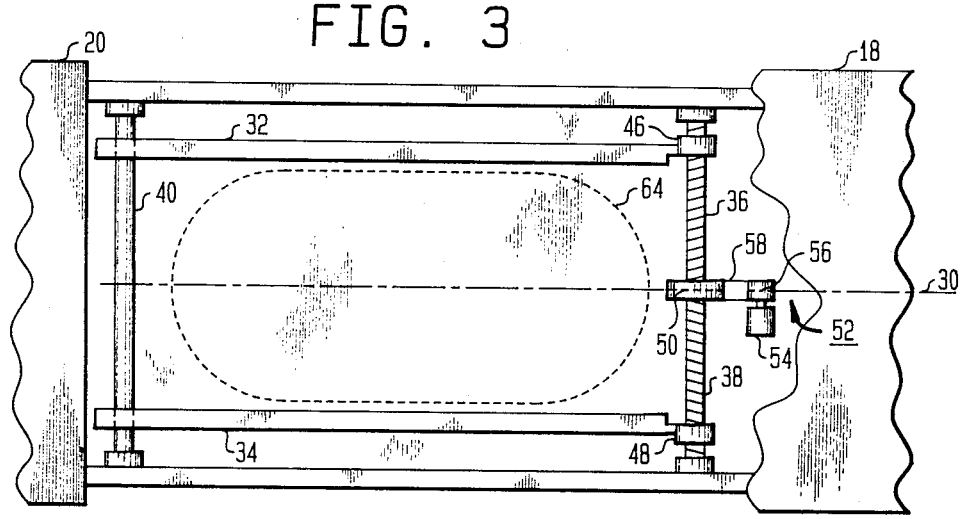

ial material, such as plexiglass ™ for example.
PATIENT TREATMENT TABLE

BACKGROUND OF THE INVENTION

1. Field of the Invention

The invention relates to a patient treatment table. A preferred field of the invention are treatment tables to perform medical treatment under a radiation providing apparatus, such as a linear accelerator.

2. Description of the prior art

A well known conventional patient treatment table is for example the Siemens Patient Treatment Table ZII. This table (a similar form is also described in German Offenlegungschrift DE-OS No. 2,153,363) comprises a base and a table plate for positioning of a patient thereon. A single spine is used to support at least one portion of the table top. However, in the area of the spine very often a clear space is required to perform medical treatment for example under a radiation providing apparatus, such as a linear accelerator. In other words, the spine arranged along the longitudinal axis of the treatment table would inhibit the treatment. However, some kind of spine is necessary to support the concerning part of the treatment table.

SUMMARY OF THE INVENTION

1. Objects

It is an object of this invention to provide a patient treatment table which despite further making use of a spine allows to perform medical treatment in the area of the spine.

2. Summary

According to this invention a patient treatment table is provided which comprises:
(a) a base;
(b) a table plate for positioning of a patient thereon;
(c) a spine for supporting at least one part of the table plate, said spine comprising two bars;
(d) means for shiftably mounting the bars of the spine on the base; and
(e) drive means for shifting the bars relative to each other beneath the table plate between a first and a second position.

According to the invention the spine is subdivided into two bars. These bars can be shifted away from each other from the original support position. This opens clear space for medical treatment between the bars, if necessary and desired.

In a preferred embodiment of the invention the table plate has a longitudinal axis and the bars in the first position are arranged parallel to each other and parallel to the longitudinal axis of the table plate. The mounting means allow shifting of the bars away from each other from the middle position perpendicular to the longitudinal axis of the table plate.

The foregoing and other objects, features and advantages of the invention will be apparent from the following more particular description of preferred embodiment of the invention, as illustrated in the accompanying drawings.

BRIEF DESCRIPTION OF THE DRAWINGS

In the drawings:

FIG. 1 is a patient treatment table according to this invention;

FIG. 2 is a top view of the interesting part of the table plate, with the spine bars in a first position;

FIG. 3 is a top view of the interesting part of the table plate, with the spine bars in the second position.

DETAILED DESCRIPTION OF THE PREFERRED EMBODIMENT

In FIG. 1 the patient treatment table 2 comprises a base 4 with a base foot 6 and a stanchion 8, and a table plate 10. The base foot 6 is located on the floor 12 directly at a treatment area 14.

The stanchion 8 is rotatably mounted on the base foot 6. The table plate 10 is mounted on the stanchion 8 by means of a plate support 16.

The table plate 10 is subdivided into plate parts 18 and 20 which are fabricated of light opaque material and plate parts 22 and 24 which are produced of light transparent material, such as plexiglass ™ for example.

All plates are kept together by means of a frame 26. The plate part 24 is also supported by a spine 28, which is arranged along the longitudinal axis 30 of the table plate.

As long as areas of the body of a patient have to be treated, which lie outside the middle position of the table plate 10 the spine 28 will not inhibit the treatment.

However, in case a treatment in the middle position becomes necessary the spine inhibits the treatment.

In order to overcome this difficulty according to this invention, the spine 28 comprises two bars 32 and 34. Furthermore, there are means provided for shiftably mounting the bars on the frame 26 and drive means for shifting the bars relative to each other beneath the table plate between a first and a second position.

According to FIGS. 2 and 3 the mounting means comprises a right thread screw 36 and a left thread screw 38. They also comprise a guide bar 40. Each bar 32 and 34 is mounted with its one end by means of a sliding hole 42 and 44, respectively on the guide bar 40. Each bar 32 and 34 is furthermore mounted with its second end by means of a nut 46 and 48, respectively on the right and left thread screws 36 and 38.

The drive means comprise a sprocket wheel 50 in the middle between the right and left thread screws 36 and 38, which sprocket wheel 50 is driven by a gear motor 52 (electrical motor 54 with drive wheel 56) via a chain 58. When rotating the right and left thread screws 36, 38 the bars 32, 34 are shifted away from each other. They travel along the screws 36 and 38 and along the guide bar 40 from a first position (middle position) as shown in FIG. 2, where they are close together into a second position, as shown in FIG. 3, where they are distant from each other.

As indicated in FIG. 2 the bars 32 and 34 in the first position are arranged parallel to each other along the longitudinal axis 30 of the table plate 10. Both bars 32 and 34 in the middle position adjoin each other. In this first position the table plate 10 provides two treatment areas, namely area 60 on the left and area 62 on the right side of the spine 28 of the table plate 10.

As illustrated in FIG. 3 the bars 32 and 34 have been shifted away from each other into a second position. In this second position both bars 32 and 34 open clear space for treatment in the middle area of the table plate 10. This area is indicated in FIG. 3 with the reference numeral 64.

Under normal treatment conditions, the patient lies with his head on plate part 20 and with his upper body part on light transparent plate part 24.

Having thus described the invention with particular reference to the preferred forms thereof, it will be obvi- ous to those skilled in the art to which the invention pertains, after understanding the invention, that various changes and modifications may be made therein without departing from the spirit and scope of the invention as defined by the claims appended hereto. For example other electrical or electromechanical driving mechanism for separating the two parallel spine bars may be provided. Also the mechanism for separating the two bars of the spine may be represented in various modifications. Furthermore, other regions of the table plate may also be provided with a spine according to this invention, if necessary or desired.

What is claimed is:

1. A patient treatment table comprising:
   (a) a base;
   (b) a fixed table plate for positioning of a patient thereon;
   (c) a spine for supporting at least one part of the table plate, said spine comprising two bars;
   (d) means for shiftably mounting the bars of the spine on the base while keeping the table plate unmoved, said means comprising a rotatable right thread screw, a rotatable left thread screw and a guide bar, one bar of the spine being mounted between the right thread screw and the guide bar, and the other bar being mounted between the left thread screw and the guide bar, such that when rotating the right and left thread screws the bars travel away fom each other; and
   (e) drive means for shifting the bars relative to each other beneath the table plate between a first and second position.

2. A patient treatment table according to claim 1, wherein the bars in the first position are close together and in the second position are distant from each other.

3. A patient treatment table according to claim 1, wherein
   (a) the table plate has a longitudinal axis; and
   (b) the bars in the first position are located close to the longitudinal axis of the table plate.

4. A patient treatment table according to claim 3, wherein the bars are located parallel to each other and to the longitudinal axis of the table plate.

5. A patient treatment table according to claim 1, wherein the bars in the first position adjoin to each other.

6. A patient treatment table according to claim 1, wherein
   (a) the table plate has a longitudinal axis; and
   (b) the bars in the second position are located far from the longitudinal axis.

7. A patient treatment table according to claim 1, wherein
   (a) the table plate has a longitudinal axis; and
   (b) the mounting means mounts the bars on the base for shifting in directions perpendicular to the longitudinal axis of the table plate.

8. A patient treatment table according to claim 7, wherein
   (a) the bars in the first position are located parallel to each other and to the longitudinal axis of the table plate; and
   (b) the mounting means mounts the bars on the base for shifting the bars away from each other perpendicular to the longitudinal axis of the table plate into positions parallel to the longitudinal axis.

9. A patient treatment table according to claim 1, wherein said drive means comprise motor driven means.

10. A patient treatment table according to claim 1 wherein the drive means comprise:
    (a) a rotatable sprocket wheel in the middle between the right and left thread screws; and
    (b) a gear motor;
    wherein the gear motor rotates the sprocket wheel such as to rotate the right and left thread screws.

* * * * *